(12) United States Patent
Wang et al.

(10) Patent No.: US 9,850,519 B1
(45) Date of Patent: Dec. 26, 2017

(54) METHOD FOR PRODUCING ALPHA-GLUCOSIDASE INHIBITORS UTILIZING PAENIBACILLUS SP

(71) Applicant: Tamkang University, New Taipei (TW)

(72) Inventors: San-Lang Wang, New Taipei (TW); Yao-Haur Kuo, New Taipei (TW); Po-Hao Shih, New Taipei (TW); Van-Bon Nguyen, New Taipei (TW); Anh-Dzung Nguyen, New Taipei (TW)

(73) Assignee: TAMKANG UNIVERSITY, New Taipei (TW)

( * ) Notice: Subject to any disclaimer, the term of this patent is extended or adjusted under 35 U.S.C. 154(b) by 0 days.

(21) Appl. No.: 15/636,641

(22) Filed: Jun. 29, 2017

(30) Foreign Application Priority Data

Nov. 17, 2016 (TW) .............................. 105137545 A (51) Int. Cl.
| | |
|---|---|
| *C12N 1/20* | (2006.01) |
| *A61K 38/00* | (2006.01) |
| *C12Q 1/25* | (2006.01) |
| *C12N 15/63* | (2006.01) |
| *C12N 15/75* | (2006.01) |
| *C12N 1/00* | (2006.01) |

(52) U.S. Cl.
CPC ................ *C12Q 1/25* (2013.01); *C12N 1/20* (2013.01); *C12N 15/63* (2013.01); *C12N 15/75* (2013.01); *C12N 1/00* (2013.01)

(58) Field of Classification Search
None
See application file for complete search history.

(56) References Cited

PUBLICATIONS

Nguyen. Biosynthesis of α-Glucosidase Inhibitors by a Newly Isolated Bacterium, *Paenibacillus* sp. TKU042 and Its Effect on Reducing Plasma Glucose in a Mouse Model. Int. J. Mol. Sci. 2017, 18, 700.*

* cited by examiner

*Primary Examiner* — Yong D Pak
(74) *Attorney, Agent, or Firm* — Chun-Ming Shih; HDLS IPR Services (57) ABSTRACT

A method for producing alpha-glucosidase inhibitors utilizing *Paenibacillus* sp., wherein utilizing a *Paenibacillus* sp. strain which is deposited at Deutsche Sammlung von Mikroorganismen and Zellkulturen GmbH (DSMZ) and numbered No. DSM 32521 to produce the alpha-glucosidase inhibitors, the *Paenibacillus* sp. Strain is cultivated in a commercial culture medium or a shrimp/crab residue-contained culture medium, and the alpha-glucosidase inhibitors is separated from a fermented supernatant. The alpha-glucosidase inhibitors have strong inhibitory activity.

4 Claims, 11 Drawing Sheets

METHOD FOR PRODUCING ALPHA-GLUCOSIDASE INHIBITORS UTILIZING *PAENIBACILLUS* SP

TECHNICAL FIELD

The present disclosure relates a method for producing alpha-glucosidase inhibitors utilizing *Paenibacillus* sp, especially a method for producing alpha-glucosidase inhibitors by using microbe and separating its fermented supernatant.

RELATED ART

Saccharides absorbed by human body would be digested from polysaccharide into oligosaccharide molecules by saliva, gastric juice, and alpha-amylase secreted by pancreas. The oligosaccharides then enter small intestine and would be digested into glucose by alpha-glucosidase of epithelial cells and gastrointestinal digestive enzyme. The concentration of blood sugar in the body would reach to the highest. Therefore, alpha-glucanase inhibitor and alpha-amylase inhibitor may be used to lower the absorption and digestion of carbohydrate significantly, and also reduce the blood sugar of the patients having noninsulin-dependent diabetes mellitus to increase after meal.

alpha-glucosidase can be found in epithelial cells in human small intestine, and may facilitate the absorption of glucose. The malfunction of alpha-glucosidase may lead to Type 2 diabetes, Pompe disease and Azoospermia.

There are two types of diabetes: Type 1 diabetes is autoimmune disease, and Type 2 diabetes is the most common chronic condition nowadays. Among high risk population of Type 2 diabetes, it is often to use glucosidase inhibitor to inhibit the absorption of saccharides. Alpha-glucosidase inhibitors, alphaGI, may ease the absorption of carbohydrates in gastrointestinal track, and lower high blood sugar after meal via inhibiting the activity of alpha-glucosidase and reducing the absorption of carbohydrates from diet as a hypoglycemic medicine to treat Type 2 diabetes. However, a conventional glucosidase inhibitor would have side effects after oral administration, such as the digestion and absorption of food would be delayed, and partial indigestive food would enter colon and be fermented by enzymes in gastrointestinal track wherein leads to uncomfortable gastrointestinal symptoms like flatulence and diarrhea.

Therefore, a solution to solve the aforementioned issues is research subject that the skilled people in the relevant industry is urgent to figure out.

DETAILED DESCRIPTIONS

To achieve the above purpose, the inventor focuses on the development of producing alpha-glucosidase inhibitors by utilizing microbe, in order to accomplish a method which is easy to access and may produce alpha-glucosidase inhibitors massively. The inventor eventually discovers the present method to produce alpha-glucosidase inhibitors utilizing *Paenibacillus* sp.

The present purpose provides a method for producing alpha-glucosidase inhibitors utilizing microbe, wherein the microbe is a strain screened from Taiwan soil which is numbered as DSM 32521 and belongs to *Paenibacillus* genus. The strain is called as DSM 32521 strain. The method comprises cultivating DSM 32521 strain in cultivation broth with oscillation for one to three days. The DSM 32521 strain may have higher production under a cultivation temperature of 30° C. After acquiring the cultivation broth which cultivated the DSM 32521 strain, a supernatant is separated from the cultivation broth using a separation method for natural product, wherein the supernatant has a significant amount of alpha-glucosidase inhibitors.

The present alpha-glucosidase inhibitor produced by the DSM 32521 strain has been proven that it does not have side effects of diarrhea like the commercial products do, and also has an efficacy of inhibiting alpha-glucosidase activity. Furthermore, the present alpha-glucosidase inhibitor has anti acid and alkali performance, and a combination of the present alpha-glucosidase inhibitor and a commercial alpha-glucosidase inhibitor creates superior efficacy.

EMBODIMENTS

In order to explain and understand the technics and procedures of the present disclosure for the examiner's courtesy, the embodiments are illustrated accompanied with figures as following.

Embodiment 1

This embodiment relates to a *Paenibacillus* sp. strain which is screened from soil by the inventor and numbered as DSM 32521 being used as a strain for production. The steps for screening include: Serial diluting soil sample with sterile water; spreading the diluted soil sample on a culture medium containing 1% squid pen powder (SPP), 0.05% $MgSO_4.7H_2O$, 0.1% $K_2HPO_4$ and 1.5% agar; cultivating the culture medium in an cultivator under 25° C. to 37° C. for one to three days, in which the temperature of 37° C. is the most preferable; obtaining the strain cultivated from the previous step and cultivating the strain in a liquid culture medium containing 1% squid pen powder, 0.05% $MgSO_4.7H_2O$ and 0.1% $K_2HPO_4$ with oscillation for three days under 25° C. to 37° C., in which the cultivation temperature of 30° C. is the most preferable; centrifuging the liquid culture medium to remove bacteria and residual solids of squid pen powder and to obtain supernatant, in which the rotation speed of 4,000 rpm to 10,000 rpm, and the rotation speed of 8,000 rpm is most preferable. Regarding measurement of bacteria growth, centrifuging the liquid culture medium with a rotation speed of 150 rpm to remove the residual solids of squid pen powder and to obtain supernatant. Absorbance of the supernatant ($OD660_{nm}$=0.38) is further detected to measure an amount of bacteria growth.

The obtained supernatant fermented by the screened strain is used to test the inhibitory activity to alpha-glucosidase. As for experimental group, the steps include: Dissolving 50 µL fermented supernatant and 50 µL alpha-glucosidase into 500 µL 0.1M NPB (N,N'-bis(naphthalen-1-yl)-N,N'-bis(phenyl)benzidine) separately as experimental group, reacting the experimental group in a water bath of 37° C. for 20 minutes, and adding 50 µL p-NPG (4-nitrophenyl β-D-glucuronide) into the experimental group in the water bath of 37° C. for another 30 minutes, and adding 650 µL 0.1M $Na_2CO_3$ into the experimental group to stop enzyme reaction. As for control group, the fermented supernatant is being replaced by deionized water. Absorbance of $OD_{410\ nm}$ for experimental group and control group is tested to calculate the inhibitory efficacy of the fermented supernatant to alpha-glucosidase (Calculation equation: [1-(experimental group/control group)]×100%). The results indicate that the inhibitory activity produced by one of the strains is the highest, and the 16S rDNA sequence of the strain is further analyzed and is found belonging to *Paenibacillus* sp., i.e. the DSM 32521 strain of the present disclosure.

Embodiment 2

This embodiment illustrates that the various parameters and conditions for cultivation affect the production of alpha-glucosidase inhibitor (abbreviated as alphaGI) utilizing *Paenibacillus* sp., and the inhibitory activities of the alpha-glucosidase inhibitor alphaGI specific to rat alpha-glucosidase (abbreviated as Rat aG) and to yeast alpha-glucosidase (Yeast aG) are tested under different conditions, in order to determine the best conditions to cultivate the DSM 32521 strain.

(1) Effect from carbon/nitrogen source: Three kinds of culture mediums are used to cultivate the DSM 32521 strain under 30° C. and pH value of 7 for several days, in order to determine the effects on the production of glucosidase inhibitor alphaGI under different cultivation conditions, such as different days and different carbon/nitrogen source, and select better carbon/nitrogen source for alpha-glucosidase inhibitors alphaGI. The first culture medium is 100 mL of 0.8% nutrient broth (abbreviate as NB) culture medium (commercial culture medium); The second culture medium is 100 mL of culture medium containing 1% shrimp head powder, 0.1% $K_2HPO_4$, 0.05% $MgSO_4.7H_2O$; and the third culture medium is 100 mL of culture medium containing 1% squid pen powder, 0.1% $K_2HPO_4$, 0.05% $MgSO_4.7H_2O$, wherein the 0.8% nutrient broth-contained culture medium is abbreviated as NB, the 1% squid pen powder-contained culture medium is abbreviated as SPP, and the 1% shrimp head powder-contained culture medium is abbreviated as SHP.

Figure 1A:
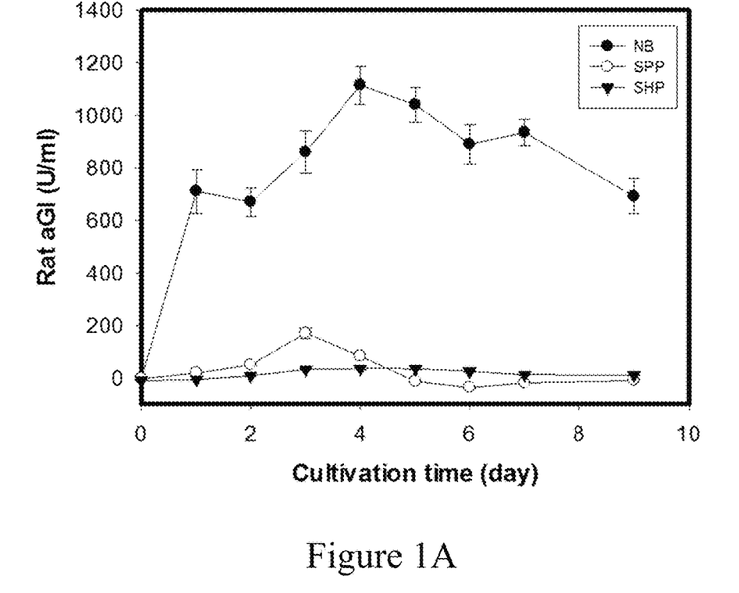
FIG. 1A indicates the results that alpha-glucosidase inhibitor produced by the present DSM 32521 strain under different carbon/nitrogen source affects rat glucosidase.
Figure 1B:
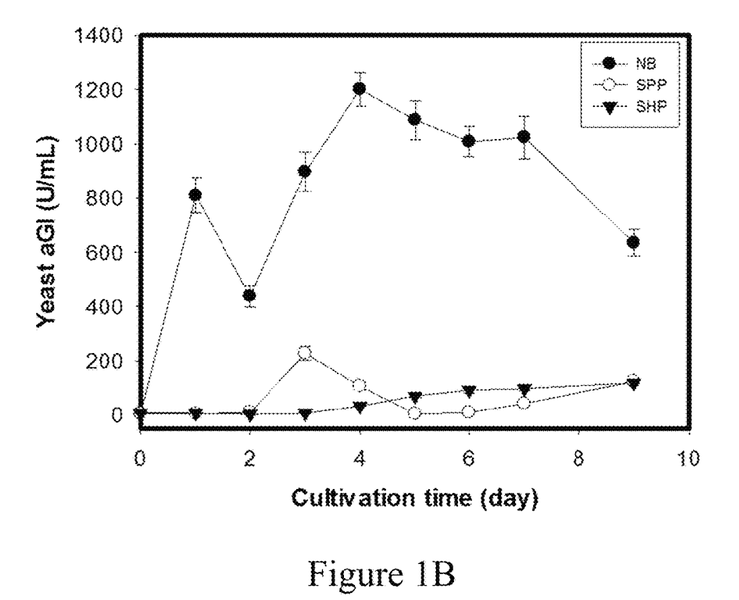
FIG. 1B indicates the results that alpha-glucosidase inhibitor produced by the present DSM 32521 strain under different carbon/nitrogen source affects yeast glucosidase.

Please refer to FIGS. 1A and 1B, the results disclose that using 0.8% NB culture medium as carbon/nitrogen source may acquire a preferable alpha-glucosidase inhibitory activity. The inhibitory activity of alpha-glucosidase increases significantly on the first day, wherein the inhibitory activity reaches the highest on the fourth day. The 0.8% NB culture medium is selected to perform the following cultivations.

(2) Effect from the cultivation temperature: The cultivation is performed under various temperatures (25° C., 30° C., and 37° C.) individually for several days. The activity of alpha-glucosidase inhibitor alphaGI is measured for each cultivation temperature on a daily basis.

Figure 2A:
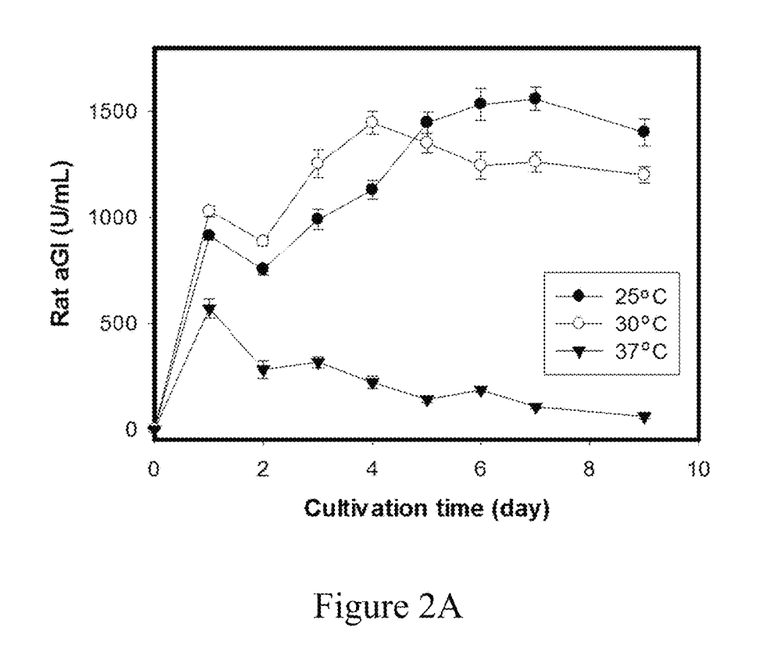
FIG. 2A indicates the results that alpha-glucosidase inhibitor produced by the present DSM 32521 strain under different temperatures affects rat glucosidase.
Figure 2B:
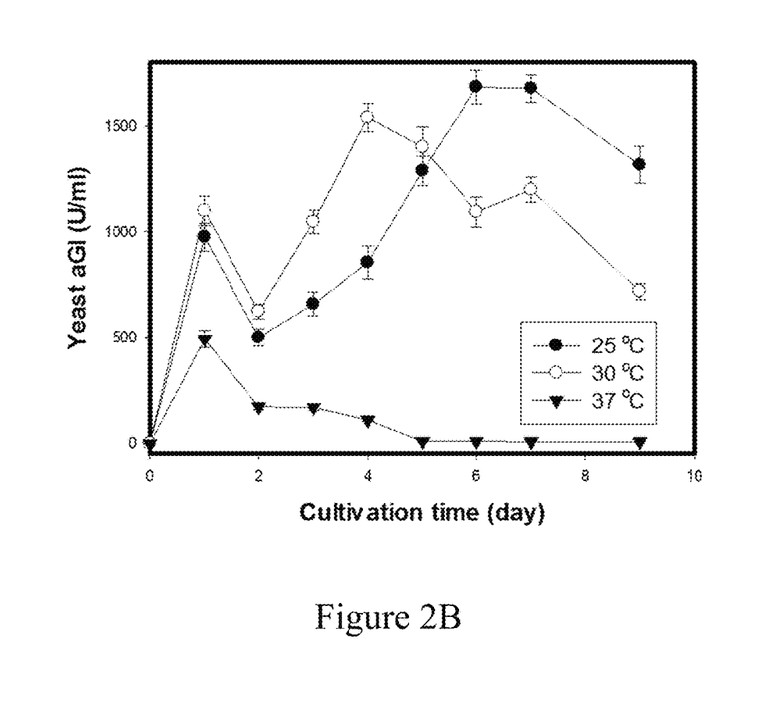
FIG. 2B indicates the results that alpha-glucosidase inhibitor produced by the present DSM 32521 strain under different temperatures affects yeast glucosidase.

Please refer to FIGS. 2A and 2B, the results disclose that the cultivation using 25° C. or 30° C. may acquire a preferable activity of alpha-glucosidase inhibitor alphaGI on the fourth to seventh day. Therefore, 30° C. is selected to perform the following cultivation.

(3) Effect from the volume of cultivation broth (aeration): The cultivation is performed in various volumes (50 mL, 100 mL, and 150 mL) of cultivation broth individually under 30° C. for several days. The activity of alpha-glucosidase inhibitor alphaGI is measured for each volume on a daily basis.

Figure 3A:
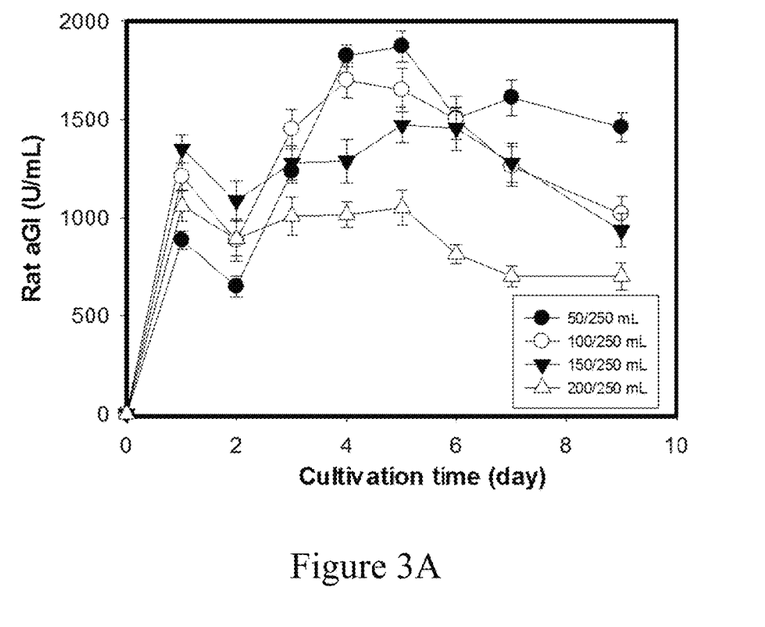
FIG. 3A indicates the results that alpha-glucosidase inhibitor produced by the present DSM 32521 strain under different volumes of cultivation broth (aeration amount) affects rat glucosidase.
Figure 3B:
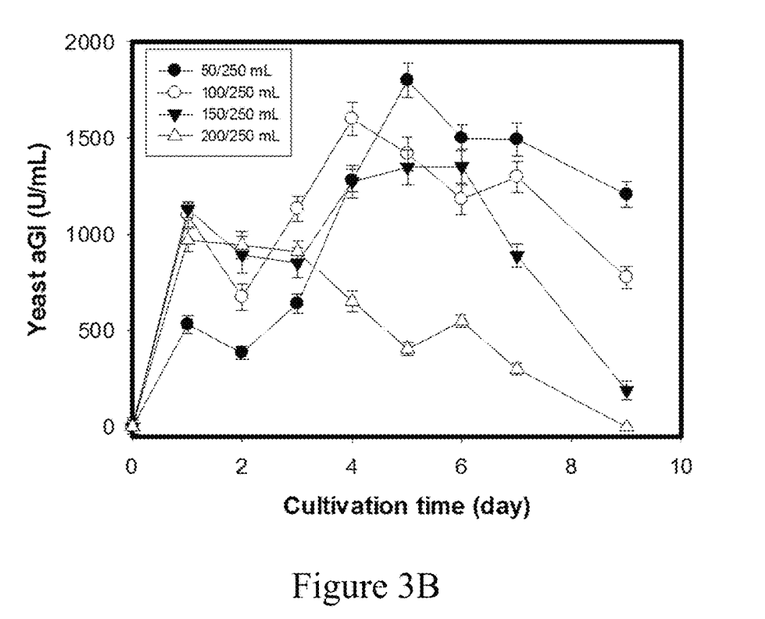
FIG. 3B indicates the results that alpha-glucosidase inhibitor produced by the present DSM 32521 strain under different volumes of cultivation broth affects yeast glucosidase.

Please refer to FIGS. 3A and 3B, the results disclose that the cultivation using 50 mL or 100 mL of cultivation broth may acquire a preferable activity of alpha-glucosidase inhibitor alphaGI on the fourth to sixth day. Therefore, the volume of 100 mL is selected to perform the following cultivation.

(4) Effect from the concentration of culture medium: The cultivation is performed in 100 mL culture medium containing various NB concentrations (0.4%, 0.8%, 1.2%, 1.6%, and 2.0%) individually under 30° C. for several days. The activity of alpha-glucosidase inhibitor alphaGI is measured for each concentration on a daily basis.

Figure 4A:
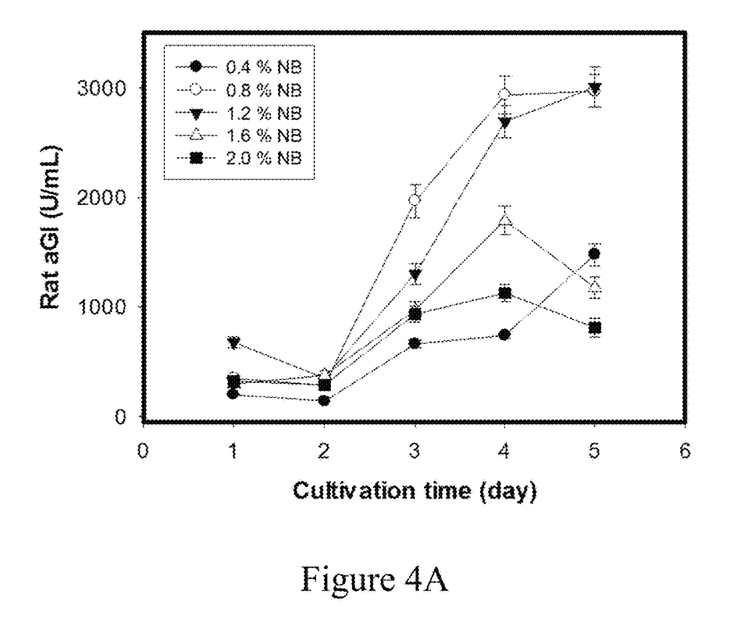
FIG. 4A indicates the results that alpha-glucosidase inhibitor produced by the present DSM 32521 strain under different concentrations of culture medium affects rat glucosidase.
Figure 4B:
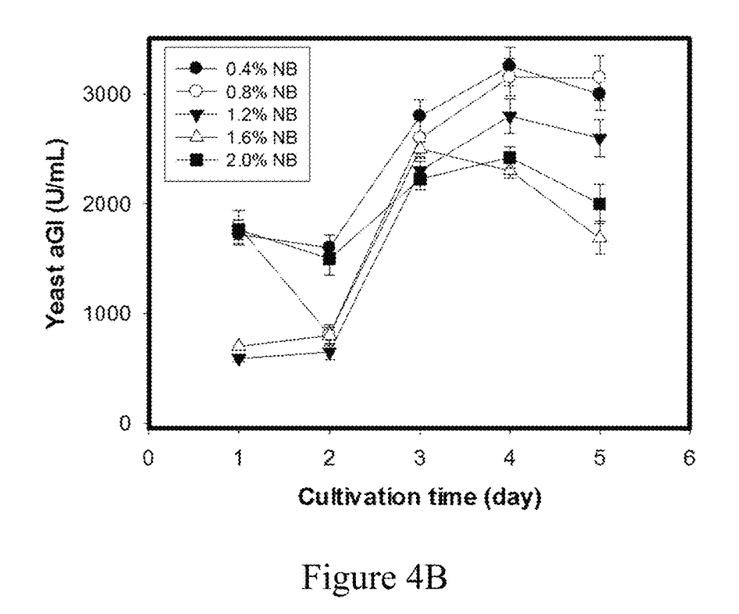
FIG. 4B indicates the results that alpha-glucosidase inhibitor produced by the present DSM 32521 strain under different concentrations of culture medium affects yeast glucosidase.

Please refer to FIGS. 4A and 4B, the results disclose that the cultivation using 0.8% to 1.2% NB concentrations may acquire a preferable activity of alpha-glucosidase inhibitor alphaGI on the fourth to fifth day.

(5) Effect from various inoculation volumes: 100 mL of 0.8% NB-contained culture medium is inoculated with various inoculation volumes (0.5 mL, 1.0 mL, 1.5 mL, 2.0 mL, 3.0 mL, and 5.0 mL) of pre-cultivation broth individually. After several days of cultivation under 30° C., the activity of alpha-glucosidase inhibitor αGI is measured for each inoculation volume on a daily basis.

Figure 5A:
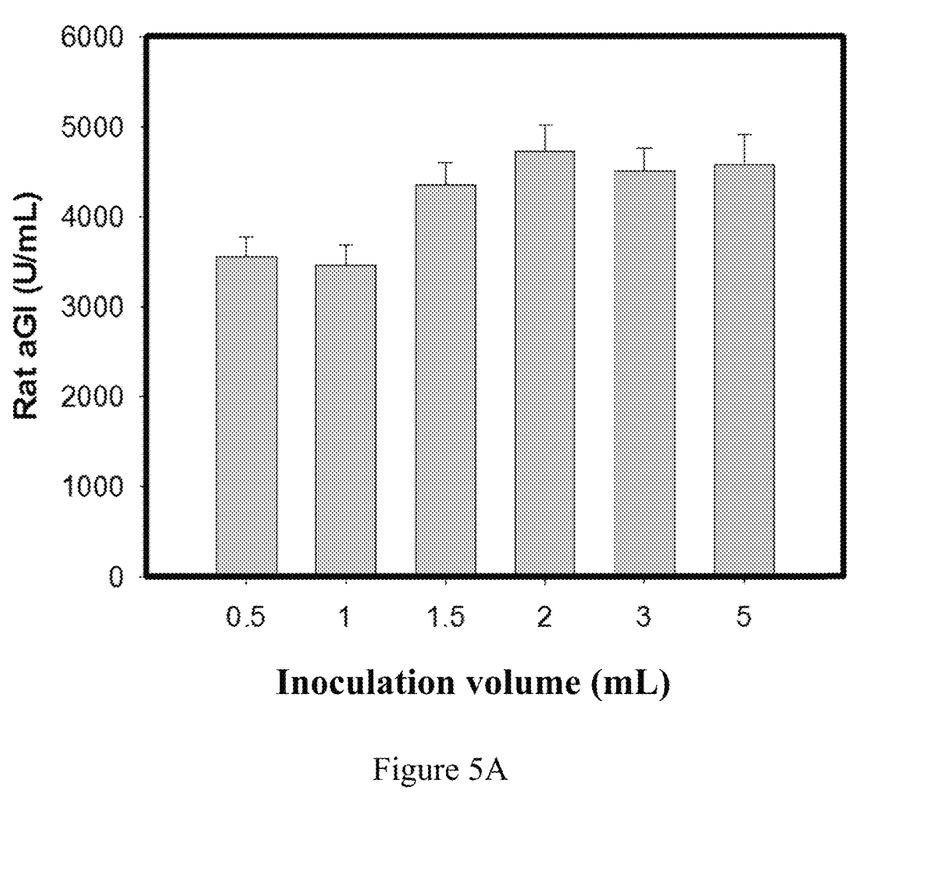
FIG. 5A indicates the results that alpha-glucosidase inhibitor produced by the present DSM 32521 strain under different inoculation volumes affects rat glucosidase.
Figure 5B:
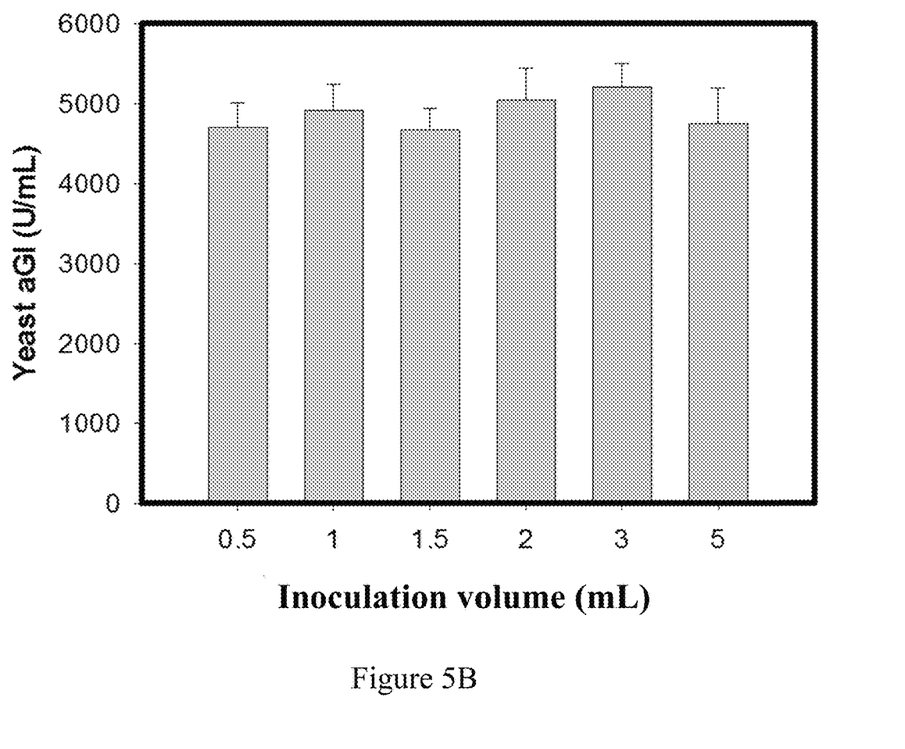
FIG. 5B indicates the results that alpha-glucosidase inhibitor produced by the present DSM 32521 strain under different inoculation volumes affects yeast glucosidase.

Please refer to FIGS. 5A and 5B, the results disclose that the amount of the inoculation volume does not play an important role to the activity of the produced alpha-glucosidase inhibitor alphaGI. Considering the cost, the following experiment is performed using a culture medium in which every 100 mL culture medium is inoculated with 2 mL pre-cultivation broth.

Embodiment 3

The present embodiment uses alpha-glucosidase inhibitor alphaGI produced by the DSM 32521 strain and one commercial diabetes medicine A (alpha-glucosidase inhibitor) sp. to inhibit rat alpha-glucosidase (Rat aG) and yeast alpha-glucosidase (Yeast aG) individually, to perform a comparison of their inhibitory activity Max % and IC 50 (the concentration of inhibitor to reach 50% inhibition ratio).

Please refer to Table 1, the Max % of inhibition ratio of alpha-glucosidase inhibitor alphaGI specific to rat alpha-glucosidase (Rat aG) is 89% and its IC50 is 101 μg/mL, and the Max % of inhibition ratio of alpha-glucosidase inhibitor alphaGI specific to yeast alpha-glucosidase (Yeast aG) is 98% and its IC50 is 81 μg/mL; the Max % of inhibition ratio of the diabetes medicine A specific to rat alpha-glucosidase (Rat aG) is 88% and its IC50 is 107 μg/mL, and the Max % of inhibition ratio of the diabetes medicine A specific to yeast alpha-glucosidase (Yeast aG) is 70% and its IC50 is 1395 μg/mL. As a result, it has been proven that the alpha-glucosidase inhibitor alphaGI produced by the DSM 32521 strain has a competitive inhibitory activity against the commercial diabetes medicine A, and the alpha-glucosidase inhibitor alphaGI produced by the DSM 32521 strain has lower IC50 which means that it requires lower concentration of the alpha-glucosidase inhibitor alphaGI produced by the DSM 32521 strain to inhibit alpha-glucosidase in practice.

TABLE 1

|  | Rat aG | | Yeast aG | |
| --- | --- | --- | --- | --- |
|  | Max (%) | IC50 (μg/mL) | Max (%) | IC50 (μg/mL) |
| alphaGI | 89 ± 4 | 101 ± 5.1 | 92 ± 3.2 | 81 ± 4.3 |
| A | 88 ± 3 | 107 + 5.5 | 70 ± 2.6 | 1395 ± 5 |

Embodiment 4

After freeze drying the alpha-glucosidase inhibitor alphaGI, the dried sample of the alpha-glucosidase inhibitor alphaGI and the diabetes medicine are used to perform animal experiments. The experimental animal is ICR mouse and the mouse is fasted for 16 hours before performing the experiments.

(1) Inhibitory Activity of Alpha-Glucosidase Inhibitors alphaGI

Experimental group: Three concentrations of alpha-glucosidase inhibitor alphaGI are prepared by dissolving the dried sample of alpha-glucosidase inhibitor alphaGI in distilled water, wherein the three concentrations are 100 mg/kg, 200 mg/kg, and 400 mg/kg, in which kg means the weight of mouse. The mouse takes in another 3 g/kg of sucrose 25 minutes after oral administration of alpha-glucosidase inhibitor alphaGI. Draw blood sample to test blood sugar level of mouse 0.5 hour, 1 hour, 1.5 hours and 2 hours after sucrose administration individually.

Control group: The mouse takes in 3 g/kg of sucrose 25 minutes after taking in distilled water of the same volume as experimental group. Draw blood sample to test blood sugar level of mouse 0.5 hour, 1 hour, 1.5 hours and 2 hours after sucrose administration individually.

Figure 6:
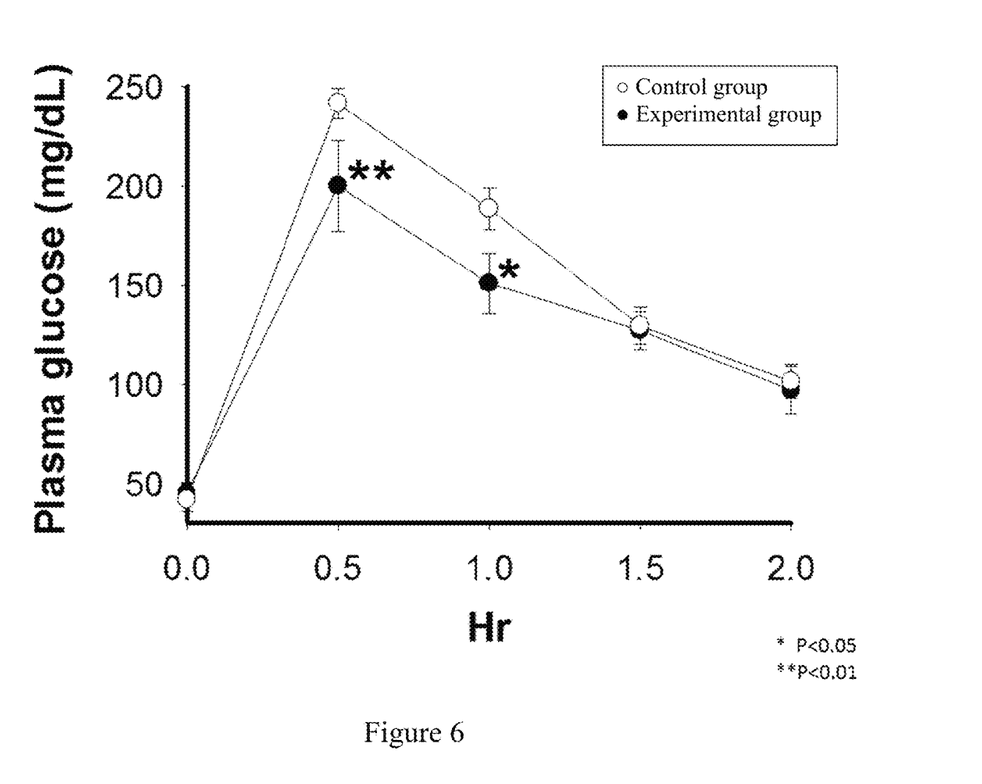
FIG. 6 indicates the results of 100 mg/kg alpha-glucosidase inhibitor of the present invention inhibiting blood sugar.
Figure 7:
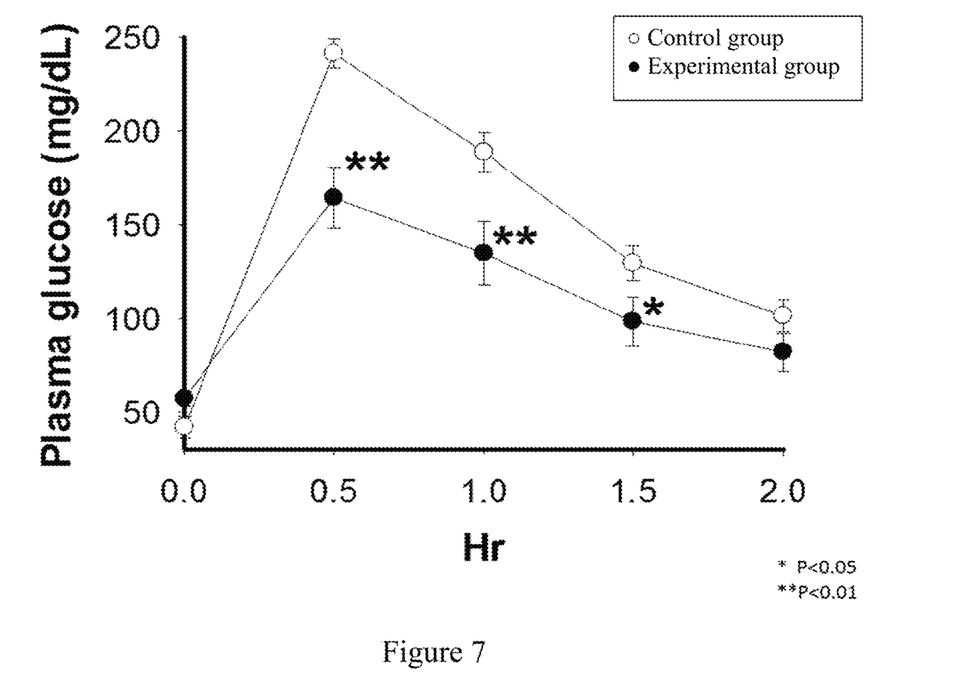
FIG. 7 indicates the results of 200 mg/kg alpha-glucosidase inhibitor of the present invention inhibiting blood sugar.
Figure 8:
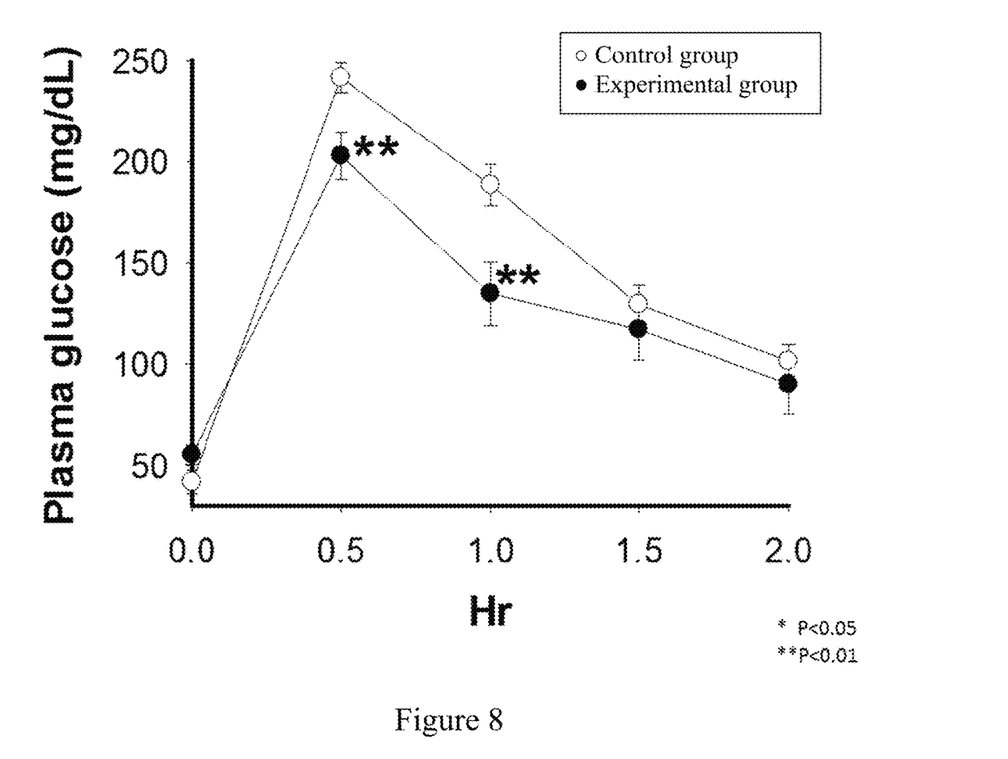
FIG. 8 indicates the results of 400 mg/kg alpha-glucosidase inhibitor of the present invention inhibiting blood sugar.

Please refer to FIGS. 6 to 8, it shows that in the experimental group, the blood sugar is being inhibited 0.5 hour after sucrose administration, wherein 200 mg/kg of alpha-glucosidase inhibitor alphaGI has the best inhibitory efficacy, and the inhibitory efficacy of the alpha-glucosidase inhibitor alphaGI is continuous and stable. In addition, the mouse does not have the side effects like diarrhea under observation.

(2) Combination of Alpha-Glucosidase Inhibitors alphaGI and Commercial Diabetes Medicine Experimental group: Based on the aforementioned experiments, the dried samples of the alpha-glucosidase inhibitor alphaGI with the concentrations of 100 mg/kg and 200 mg/kg respectively would be dissolved in distilled water together with 12.5 mg of the diabetes medicine A (i.e. Acarbose) separately. The mouse takes in another 3 g/kg of sucrose 25 minutes after oral administration of the aforementioned two combinations. Draw blood sample to test blood sugar level of mouse 0.5 hour, 1 hour, 1.5 hours and 2 hours after sucrose administration individually.

Control group: The mouse takes in 3 g/kg of sucrose 25 minutes after taking in distilled water of the same volume as experimental group. Draw blood sample to test blood sugar level of mouse 0.5 hour, 1 hour, 1.5 hours and 2 hours after sucrose administration individually.

Figure 9:
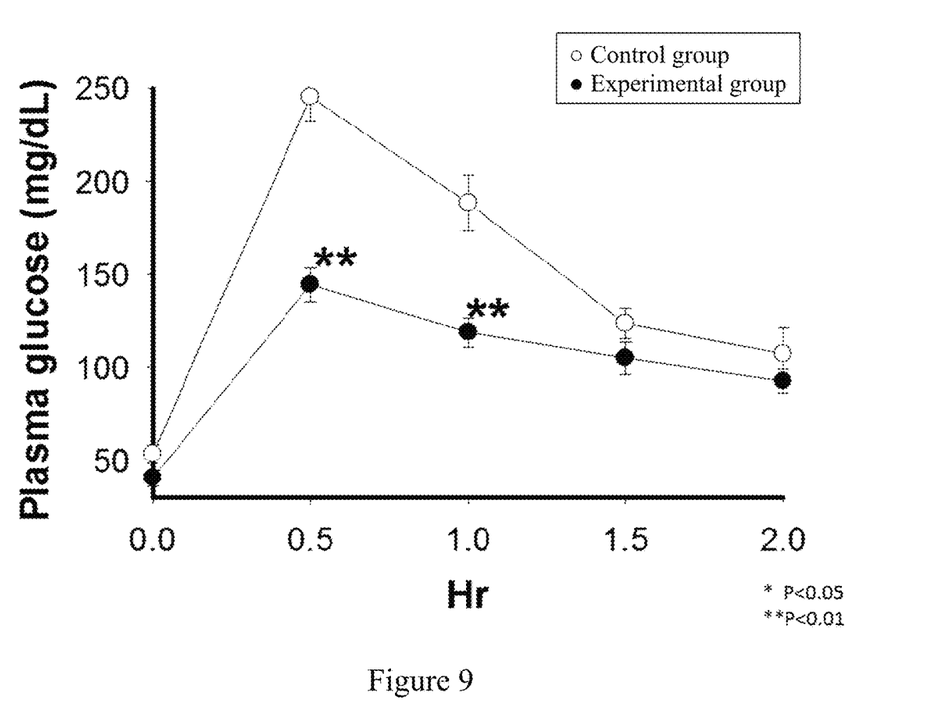
FIG. 9 indicates the results of a combination inhibiting blood sugar, and the combination is 100 mg alpha-glucosidase inhibitor and 12.5 mg diabetes medicine of the present invention.
Figure 10:
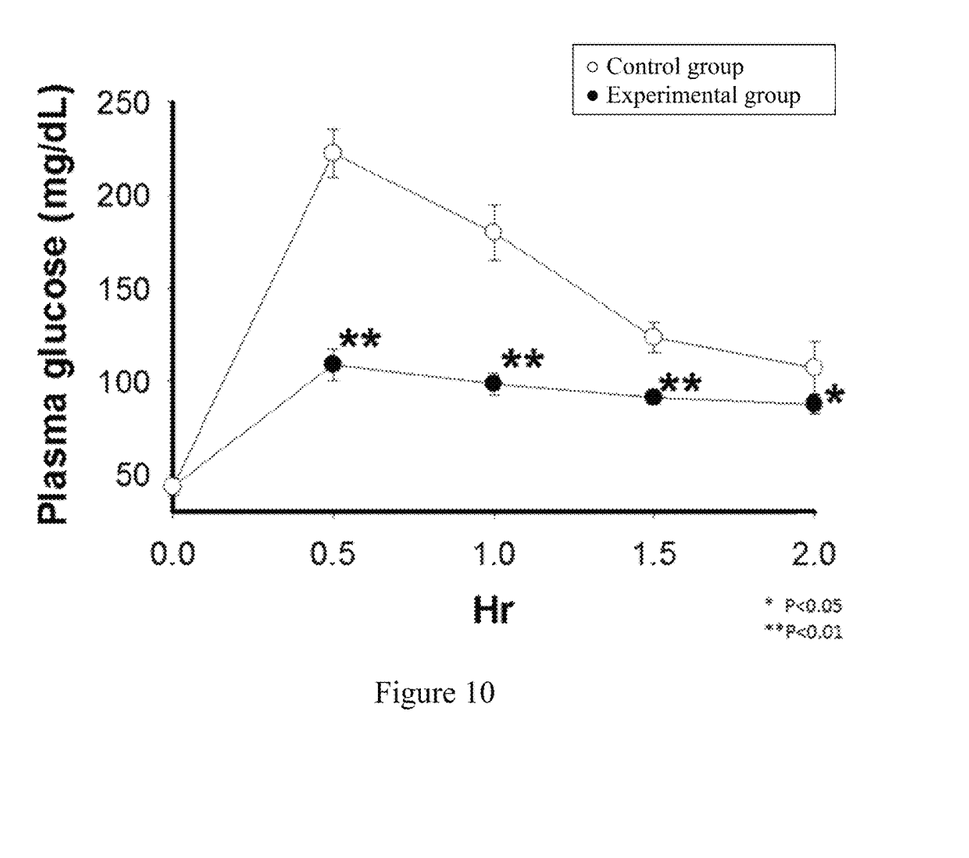
FIG. 10 indicates the results of a combination inhibiting blood sugar, and the combination is 200 mg alpha-glucosidase inhibitor and 12.5 mg diabetes medicine of the present invention.

Please refer to FIGS. 9 and 10, it shows that experimental group which combines with the diabetes medicine A has multiplicative efficacy in controlling blood sugar.

Based on the results of the aforementioned experiment, the combination of alpha-glucosidase inhibitors alphaGI and the diabetes medicine A reduces blood sugar level much better than the usage of alpha-glucosidase inhibitors alphaGI solely, and has a great and continuous efficacy to reduce blood sugar. Under observation, the mouse does not have any side effects. Therefore, the alpha-glucosidase inhibitor alphaGI can be used with commercial hypoglycemic medicines to achieve a multiplicative efficacy of lowering blood sugar and reducing side effects from the commercial medicines by reducing the dosage of commercial hypoglycemic medicines.

The aforementioned descriptions are preferred embodiments of the present disclosure and do not limit the scope of the present disclosure. Therefore, simple and equivalent variation and revision based on the present claim scope and the contents of present specification would fall within the claim scope of the present disclosure.

[Deposit of Biological Material]
Deposit Information
Leibniz Institute DSMZ-German Collection of Microorganisms and Cell Cultures (DSMZ)
May 26, 2017, DSM 32521
Food Industry Research and Development Institute of Bioresource Collection and Research Center (BCRC)
Oct. 27, 2016, BCRC 910751

The invention claimed is:

1. Method for producing alpha-glucosidase inhibitor utilizing *Paenibacillus* sp. comprising a *Paenibacillus* sp. strain which is a DSM 32521 strain deposited at Leibniz Institute DSMZ-German Collection of Microorganisms and Cell Cultures (DSMZ), and is used for production, wherein the DSM 32521 strain is cultivated under 25° C. to 37° C. for at least three days, and then is centrifuged using a rotation speed of 4000 rpm to 10000 rpm to acquire a supernatant which has alpha-glucosidase inhibitor, and wherein a carbon/nitrogen source to cultivate the DSM 32521 strain is 100 ml of 0.8% nutrient broth-contained culture medium.

2. The method for producing alpha-glucosidase inhibitor of claim 1, wherein the cultivation temperature is 30° C.

3. The method for producing alpha-glucosidase inhibitor of claim 1, wherein another carbon/nitrogen source to cultivate the DSM 32521 strain is 100 mL culture medium containing 1% shrimp head powder, 0.1% $K_2HPO_4$, and 0.05% $MgSO_4.7H_2O$.

4. The method for producing alpha-glucosidase inhibitor of claim 1, wherein another carbon/nitrogen source to cultivate the DSM 32521 strain is 100 mL culture medium containing 1% squid pen powder, 0.1% $K_2HPO_4$, and 0.05% $MgSO_4.7H_2O$.

* * * * *

UNITED STATES PATENT AND TRADEMARK OFFICE
CERTIFICATE OF CORRECTION

PATENT NO. : 9,850,519 B1
APPLICATION NO. : 15/636641
DATED : December 26, 2017
INVENTOR(S) : San-Lang Wang et al.

Page 1 of 1

It is certified that error appears in the above-identified patent and that said Letters Patent is hereby corrected as shown below:

On the Title Page

Item (72) Inventors:
Change "Van-Bon Nguyen, New Taipei (TW)" to --Van-Bon Nguyen, Buon Ma Thout City (VN)--;
Change "Anh-Dzung Nguyen, New Taipei (TW)" to --Van-Bon Nguyen, Buon Ma Thout City (VN)--.

Signed and Sealed this
Nineteenth Day of February, 2019

Andrei Iancu
*Director of the United States Patent and Trademark Office*